United States Patent
Cima et al.

(10) Patent No.: US 9,918,656 B2
(45) Date of Patent: Mar. 20, 2018

(54) IMPLANTABLE MAGNETIC RELAXATION SENSORS AND METHODS OF MEASURING A SENSOR'S CUMULATIVE EXPOSURE TO A BIOMARKER

(75) Inventors: Michael J. Cima, Winchester, MA (US); Paul Huang, Boston, MA (US); Yibo Ling, Brooklyn, NY (US); Terrence Pong, San Francisco, CA (US); Christophoros C. Vassiliou, Cambridge, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 548 days.

(21) Appl. No.: 13/806,348

(22) PCT Filed: Jun. 27, 2011

(86) PCT No.: PCT/US2011/042022
§ 371 (c)(1),
(2), (4) Date: Feb. 25, 2013

(87) PCT Pub. No.: WO2011/163661
PCT Pub. Date: Dec. 29, 2011

(65) Prior Publication Data
US 2013/0150707 A1    Jun. 13, 2013

Related U.S. Application Data

(60) Provisional application No. 61/358,449, filed on Jun. 25, 2010.

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0031* (2013.01); *A61B 5/14546* (2013.01);
(Continued)

(58) Field of Classification Search
CPC .......... A61B 2562/0285; A61B 5/0031; A61B 5/055; A61B 5/14546
(Continued)

(56) References Cited

U.S. PATENT DOCUMENTS 5,483,958 A * 1/1996 Merberg ................... G01J 1/58
250/368
6,670,115 B1 * 12/2003 Zhang ............................ 435/5
(Continued)

OTHER PUBLICATIONS

Daniel, K.D. et al., "Multi-Reservoir Device for Detecting a Soluble Cancer Biomarker," Lab Chip 7, 1288-1293 (2007).
(Continued)

*Primary Examiner* — Baisakhi Roy
(74) *Attorney, Agent, or Firm* — Eversheds Sutherland (US) LLP

(57) ABSTRACT

An implantable magnetic relaxation sensor is provided that comprises superparamagnetic nanoparticies functionalized with one or more agents that bond with a biomarker of interest. The sensor is configured for minimally-invasive implantation into a human or animal, and is configured to indicate the implanted sensor's cumulative exposure to the biomarker of interest by analysis using magnetic resonance relaxometry.

16 Claims, 17 Drawing Sheets

(51) Int. Cl.
*A61B 5/145* (2006.01)
*G01R 33/56* (2006.01)
*G01R 33/30* (2006.01)
*G01R 33/50* (2006.01)

(52) U.S. Cl.
CPC .. *G01R 33/5601* (2013.01); *A61B 2562/0285* (2013.01); *G01R 33/302* (2013.01); *G01R 33/50* (2013.01)

(58) Field of Classification Search
USPC ........................... 600/420; 424/9.2; 623/2.17
See application file for complete search history.

(56) References Cited

U.S. PATENT DOCUMENTS

| | | | |
|---|---|---|---|
| 2005/0049472 | A1 | 3/2005 | Manda et al. |
| 2007/0161884 | A1* | 7/2007 | Black ............... A61B 5/0031 600/407 |
| 2008/0305048 | A1 | 12/2008 | Josephson et al. |
| 2009/0004113 | A1* | 1/2009 | Wolf ........................... 424/9.2 |
| 2009/0220434 | A1 | 9/2009 | Sharma |
| 2009/0299155 | A1 | 12/2009 | Yang et al. |
| 2009/0324494 | A1* | 12/2009 | Ham et al. ................. 424/1.65 |
| 2009/0326595 | A1 | 12/2009 | Brockway |
| 2010/0072994 | A1 | 3/2010 | Lee et al. |
| 2010/0200428 | A1* | 8/2010 | Choi et al. ................ 205/777.5 |
| 2011/0127438 | A1* | 6/2011 | Cabral, Jr. ............ G01T 1/026 250/370.07 |
| 2011/0163661 | A1 | 7/2011 | Lee et al. |
| 2011/0166043 | A1* | 7/2011 | Nagy ....................... C07K 7/02 506/18 |
| 2011/0244048 | A1* | 10/2011 | Amiji et al. ................. 424/493 |
| 2012/0003160 | A1* | 1/2012 | Wolf et al. .................. 424/9.32 |
| 2012/0223705 | A1* | 9/2012 | Lowery ................ A61B 5/055 324/307 |
| 2012/0265296 | A1* | 10/2012 | McNamara et al. ......... 623/2.17 |

OTHER PUBLICATIONS

Kim, G.Y. et al., "Magnetic Relaxation Switch Detection of Human Chorionic Gonadotrophin," Bioconjugate Chem.18, 2024-2028 (2007).
Taktak, S. et al., "Multiparameter Magnetic Relaxation Switch Assays," Anal. Chem. 79, 8863-8869 (2007).
Tsourkas, A. et al., "Magnetic Relaxation Switch Immunosensors Detect Enantiomeric Impurities," Angew. Chem. Int'l Ed. Engl. 43, 2395-2399 (2004).
Perez, J.M. et al., "Magnetic Relaxation Switches Capable of Sensing Molecular Interactions," Nat. Biotechnol. 20, 816-820 (2002).
Perez, J.M. et al., "Use of Magnetic Nanoparticles as Nanosensors to Probe for Molecular Interactions," Chembiochem. 5 261-264 (2004).
Perez, J.M. et al., "DNA-Based Magnetic Nanoparticle Assembly Acts as a Magnetic Relaxation Nanoswitch Allowing Screening of DNA-Cleaving Agents," J. Am. Chem. Soc. 124, 2856-2857 (2002).
Sun, E.Y. et al., "Continuous Analyte Sensing with Magnetic Nanoswitches," Small 2, 1144-1147 {2006).
Wunderbaldinger, P. et al.,"Crosslinked Iron Oxides (CLIO): A New Platform for the Development of Targeted MR Contrast Agents," Acad. Radiol 9 Suppl 2, S304-306 (2002).
Zhao, M. et al., "Magnetic Sensors for Protease Assays," Angew. Chem. Int'l. Ed. Engl. 42, 1375-1378 (2003).
Daniel, K.D. et al., "Implantable Diagnostic Device for Cancer Monitoring," Biosens. Bioelectronics 24, 3252-3257 (2009).
Ling, Y. et al., "Implantable Magnetic Relaxation Sensors Measure Cumulative Exposure to Cardiac Biomakers," Nature Biotechnology, 1-6 (2011).

* cited by examiner

IMPLANTABLE MAGNETIC RELAXATION SENSORS AND METHODS OF MEASURING A SENSOR'S CUMULATIVE EXPOSURE TO A BIOMARKER

CROSS-REFERENCES TO RELATED APPLICATIONS

This application is a national phase entry of PCT Patent Application No. PCT/US2011/042022, filed on Jun. 27, 2011, designating the United States of America, and claims priority to U.S. Provisional Application No. 61/358,449, filed on Jun. 25, 2010, which is incorporated by reference herein in its entirety.

STATEMENT REGARDING FEDERALLY SPONSORED RESEARCH OR DEVELOPMENT

This invention made with government support under Grant No. U54 CA119349 awarded by the National Institutes of Health. The government has certain rights in the invention.

BACKGROUND

The physiological levels of molecular biomarkers can be regarded as time-varying continuous signals. However, clinicians seldom take advantage of this temporal information in making diagnostic and prognostic decisions. Biomarker measurements are often made at single time points, which do not adequately capture the dynamics of the underlying signal if they miss transient changes occurring between measurements. For instance, levels of serum cardiac troponin I (cTnI), creatinine kinase (the CK-MB isoform) and myoglobin elevate and return to baseline in a stereotyped manner after acute myocardial infarction (MI). A given measured value could correspond to either the early or late phase of biomarker release.

Most MIs are characterized by symptoms of severe discomfort. However, a significant minority, defined as unrecognized MIs, are accompanied by minimal or no symptoms. The 30-year follow-up of the Framingham Heart Study reported that 28% and 35% of MIs are unrecognized in men and women, respectively. Gutterman D. D. Silent myocardial ischemia, *Circ. J.* 73, 785-797 (2009). However, current standards for detecting unrecognized MIs rely primarily on electrocardiographic surveillance. Results vary markedly between such studies because of differing electrocardiographic criteria. Patients at high risk for unrecognized MIs are followed periodically by their cardiologists but MIs timed between these visits can go unnoticed.

Accordingly, it would be desirable to provide a sensor that reports on integrated MI biomarker levels throughout these intervals to identify these previously undetectable infarcts.

SUMMARY

Implantable magnetic relaxation sensors are provided that are capable of integrating biomarker levels over time. The signal from such a device may correspond to the entirety of biomarker release long after a pathologic event has occurred, and even after the concentrations have returned to baseline. Clinical recognition of these events would have a tremendous impact on subsequent therapeutic decisions, affording physicians the opportunity to initiate treatment of MI.

In one aspect, a method is provided for analyzing biomarkers for myocardial infarction in a patient. The method includes contacting interstitial fluid in the patient with a sensor for at least one biomarker for myocardial infarction; and reading the sensor to the assess the presence of the at least one biomarker. It has now been advantageously discovered that such biomarkers can be detected in the interstitial fluid of a patient.

In another aspect, an implantable magnetic relaxation sensor is provided that comprises superparamagnetic nanoparticles functionalized with one or more agents that bond with a biomarker of interest. The sensor is configured for minimally-invasive implantation into a human or animal, and is configured to indicate the implanted sensor's cumulative exposure to the biomarker of interest by analysis using magnetic resonance relaxometry.

In another aspect, an implantable magnetic relaxation sensor is provided that comprises superparamagnetic nanoparticles functionalized with one or more antibodies for myoglobin, cTnI, CK-MB, or a combination thereof. The sensor is configured to indicate the sensor's cumulative exposure to myoglobin, cTnI, CK-MB, or a combination thereof after the sensor has been implanted and the sensor is analyzed using magnetic resonance relaxometry.

In yet another aspect, a method is provided for sensing a cumulative exposure of a biomarker of interest in a person or animal. The method includes implanting at an implantation site in the person or animal a magnetic relaxation sensor comprising superparamagnetic nanoparticles functionalized with one or more agents for bonding to the biomarker of interest. The method further includes directing electromagnetic energy at the implantation site and analyzing a spin relaxation property of the sensor to determine the cumulative exposure to the biomarker of interest.

In still another aspect, a method is provided for diagnosing the occurrence of a myocardial infarction in a person or animal. The method includes identifying a patient having a high risk of a future myocardial infarction; and implanting at an implantation site in the patient a magnetic relaxation sensor which comprises superparamagnetic nanoparticles comprising one or more antibodies for myoglobin, cTnI CK-MB, or a combination thereof.

BRIEF DESCRIPTION OF THE SEVERAL DRAWING VIEWS

DETAILED DESCRIPTION

Figure 1:
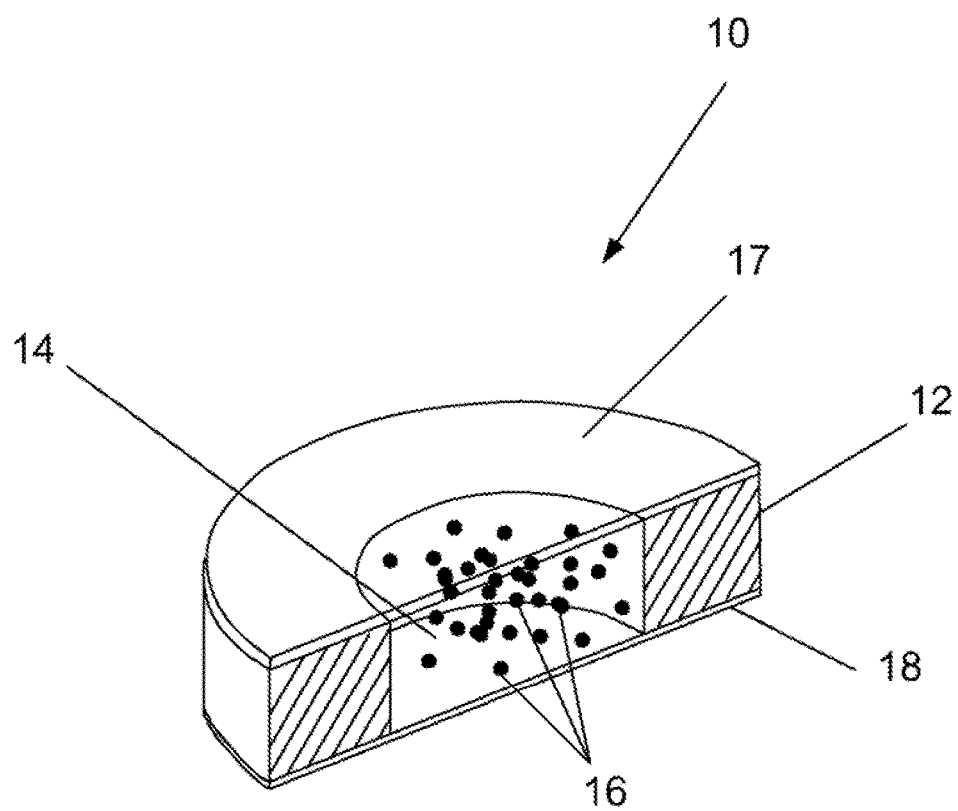
FIG. 1 is a section view, illustrating an implantable magnetic relaxation sensor according to one or more embodiments of the present disclosure.

Implantable magnetic relaxation sensors are provided that are capable of integrating biomarker levels over time. The signal from such a device may correspond to the entirety of biomarker release long after a pathologic event has occurred, and even after the concentrations have returned to baseline. Clinical recognition of these events would have a tremendous impact on subsequent therapeutic decisions, affording physicians the opportunity to initiate treatment of MI.

Sensors

Sensors are provided for indicating the sensor's cumulative exposure to a biomarker of interest. The term "biomarker" refers to an endogenous substance that is indicative of a biological state. For example, a biomarker may be a substance produced by a body or present in the body that corresponds to the occurrence of a particular disease state. The sensors may be used to detect a variety of small molecules including proteins, nucleic acids, oligonucleotides, peptides, receptors, ligands and antibodies. In an exemplary embodiment, the biomarker of interest may be a cardiac biomarker such as myoglobin, cardiac troponin I (cTnI), creatinine kinase (particularly, the CK-MB isoform), or a combination thereof.

The term "cumulative exposure" as used herein refers to a sensor's ability to indicate a cumulative or total amount of the biomarker present in the sensor's environment over a period of time as opposed to a sensor's ability to indicate the amount of the biomarker present in the sensor's environment at the time of the measurement. For example, the sensor may be configured to indicate the total amount of biomarker that was exposed to the sensor over the period of time in which the sensor is implanted in a patient, such as a human or animal.

In an exemplary embodiment, the sensor is implantable. The implantable sensor may be wholly deployable and implantable within a patient. The term "implantable" as used herein refers to a device that is configured for implantation. That is, the device is to be introduced into a subject's body by a surgical or medical procedure and remain there after the procedure. The term "wholly deployable" or "wholly deployed" and "wholly implanted" or "wholly implantable" means that there is not a portion of the sensor device that extends out of the patient transcutaneously or from an anatomical orifice. For example, the device may be sized and shaped to be wholly deployed in the body of a human or animal and to remain deployed for a period of time, such as 30 days or more. Advantageously, in some embodiments, the sensor may be wholly deployed in vivo and subjected to repeated measurements thereby overcoming the problems associated with repetitive invasive measurement procedures. The device also may have suitable sterility, biocompatibility, and physical and/or chemical integrity to be implanted and remain implanted over the intended duration of use of the device.

In a preferred embodiment, the sensor may be of a size and shape enabling the sensor to be implanted subcutaneously. In certain embodiments, the sensor may further be of a size and shape enabling the sensor to be implanted subcutaneously by a minimally invasive procedure, such as via a needle, cannula, catheter, trochar, or combination thereof. The term "minimally invasive procedure" and the like as used herein has its usual meaning and refers to a surgical procedure that is less invasive than an open surgical procedure.

In an exemplary embodiment, an implantable magnetic relaxation sensor may include superparamagnetic nanoparticles functionalized with one or more agents that bond with a biomarker of interest. The superparamagnetic nanoparticles may comprise, for example, iron oxide. The one or more agents may be suitable for forming a strong bond with the biomarker of interest such that the biomarker of interest remains bonded with the nanoparticles and does not diffuse out of the sensor as the concentration of the biomarker in the environment around the sensor subsides over time. The term "bond" as used herein refers to a strong interaction between the biomarker and agent that allows the biomarker to remain in the sensor despite changes in the environmental concentration of the biomarker and encompasses ionic bonds, covalent bonds, and other intermolecular or intramolecular interactions. In an exemplary embodiment, the agent may comprise an antibody, such as one or more antibodies for myoglobin, cTnI, CK-MB, or a combination thereof. The agent may also comprise an aptamer or DNA.

In an exemplary embodiment, the sensor may further be configured for minimally-invasive implantation into a human or animal and be configured to indicate the implanted sensor's cumulative exposure to the biomarker of interest by analysis using magnetic resonance relaxometry. For example, the superparamagnetic nanoparticles aggregate about the biomarker and alter the transverse relaxivity ($T_2$) of surrounding water protons, for example, water protons present within the sensor.

Accordingly, in an embodiment in which the biomarker of interest is myoglobin, cTnI, CK-MB, or a combination thereof, the sensor may comprise superparamagnetic nanoparticles that are functionalized with antibodies for myoglobin, cTnI, CK-MB, or a combination thereof, and the sensor may be configured to indicate the sensor's cumulative exposure to myoglobin, cTnI, CK-MB, or a combination thereof after the sensor has been implanted and the sensor is analyzed using magnetic resonance relaxometry. Methods for functionalizing nanoparticles are known in the art.

As illustrated in FIG. 1, the sensor 10 may include a sensor body 12 having at least one reservoir 14 and a plurality of superparamagnetic nanoparticles 16 that are contained within the at least one reservoir 14. The nanoparticles 16 may be functionalized with agents suitable for bonding with the biomarker of interest and may be retained within the at least one reservoir 14 by one or more size-exclusion membranes 17, 18. The nanoparticles 16 may be provided as a suspension in a liquid or solution, such as an aqueous solution, within the reservoir 14.

The sensitivity of the sensor 10 may be adjusted or tuned to a sensitivity useful for the intended application of the sensor 10. The sensitivity may be tuned, for example, by adjusting the transport characteristics of the sensor and/or adjusting the nanoparticle chemistry. For example, the transport characteristics of the sensor may be adjusted by selection of the membrane composition, pore size, and or surface area. The nanoparticle chemistry may be adjusted by selection of the agent composition, particle size, and the amount of agent used. In some embodiments, the sensor is sensitive to cTnI in a range of 10-100 ng/mL, is sensitive to myoglobin in a range of 100 ng/mL to 1 μg/mL, and/or is sensitive to CK-MB in a range of 100 ng/mL to 1 μg/mL.

Methods

Methods are provided for sensing a cumulative exposure of a biomarker of interest in a person or animal. The method may include implanting at an implantation site in the person or animal a magnetic relaxation sensor comprising superparamagnetic nanoparticles functionalized with one or more agents for bonding to the biomarker of interest. After implantation, electromagnetic energy may be directed at the site, and a spin relaxation property of the sensor may be analyzed to determine the sensor's cumulative exposure to the biomarker of interest. For example, the transverse relaxivity ($T_2$) of water protons in the sensor may be analyzed.

The implantation site may be any suitable tissue site. For example, the tissue site may be one selected to expose the sensor to interstitial fluid. In an exemplary embodiment, the sensor may be implanted at a subcutaneous implantation site. The sensor may be implanted at the implantation site by a minimally invasive implantation procedure.

In an exemplary embodiment, the one or more agents may be one or more antibodies, such as antibodies for myoglobin, cTnI, CK-MB, or a combination thereof. In such an embodiment, the sensor may be configured to indicate the sensor's cumulative exposure to myoglobin, cTnI, CK-MB, or a combination thereof after the sensor has been implanted and the sensor is analyzed using magnetic resonance relaxometry. The method may further comprise analyzing the sensor's cumulative exposure to myoglobin, cTnI, CK-MB, or a combination thereof to determine if a myocardial infarction occurred.

Methods are also provided for analyzing biomarkers for myocardial infarction in a patient. The method may include contacting interstitial fluid in the patient with a sensor for at least one biomarker for myocardial infarction, and reading the sensor to the assess the presence of the at least one biomarker. In an exemplary embodiment, the biomarker of interest may be a cardiac biomarker such as myoglobin, cardiac troponin I (cTnI), creatinine kinase (particularly, the CK-MB isoform), or a combination thereof. The sensor may be configured to indicate the implanted sensor's cumulative exposure to the biomarker by analysis using magnetic resonance relaxometry. The sensor may be implanted subcutaneously in the patient. In certain embodiments, the sensor may be implanted subcutaneously at a location remote to the heart in the patient, such as in the patient's flank.

Methods are also providing for diagnosing the occurrence of a myocardial infarction in a person or animal. The method includes identifying a patient having a high risk of a future myocardial infarction; and implanting at an implantation site in the patient a magnetic relaxation sensor which comprises superparamagnetic nanoparticles functionalized with one or more antibodies for myoglobin, cTnI, CK-MB, or a combination thereof. The patient may be identified, for example, by evaluating the patient's Thrombolysis in Myocardial Infarction (TIMI) score from a previous myocardial infarction. The method may further include directing electromagnetic energy to the sensor at the implantation site, and analyzing a spin relaxation property, such as a transverse relaxivity, of the sensor to determine the cumulative exposure to myoglobin, cTnI, CK-MB, or a combination thereof. The method may also include analyzing the cumulative exposure of the sensor to myoglobin, cTnI, CK-MB, or a combination thereof to determine if a myocardial infarction has occurred in the patient.

In any of the methods described herein, the steps of directing electromagnetic energy to the sensor at the implantation site and analyzing a spin relaxation property can carried out using commercially available equipment and analytical software.

Any of the previously-described sensors may be used in the methods described herein. For example, in some embodiments, the sensor is sensitive to cTnI in a range of 10-100 ng/mL, is sensitive to myoglobin in a range of 100 ng/mL to 1 μg/mL, and/or is sensitive to CK-MB in a range of 100 ng/mL to 1 μg/mL.

New high-sensitivity troponin assays will lead to an increasing population of patients identified with elevated troponins of nonischemic etiology. Additional assays may be developed to help physicians distinguish between acute coronary syndromes and other causes. In vivo diagnostic magnetic sensor relaxation measurements may prove to be especially useful in discriminating between troponin elevations caused by transient tachyarrhythmias and sustained ischemic episodes. These integrative sensors may be engineered to have lower sensitivity so that they do not saturate upon total exposure to analyte released during and after an MI. The troponin sensor discussed here, for example, has sensitivity in the ng/ml range but could be engineered for even higher sensitivity to the pg/ml range of the newest troponin assays.

Longer-term biomarker accumulations should be feasible as long as device saturation characteristics and antibody stability are taken into consideration. Thus, integrative sensors may provide prognostic value as sentinels in high-risk patients and for the detection of unrecognized MIs. The ability to track cumulative biomarkers in vivo can be advantageous for its ability to capture transient events, which are frequently missed with serial testing. Furthermore, the described sensors can be useful in research as a tool for monitoring biomarkers in small animals in which serial blood draws may not be feasible.

The present methods and devices may be further understood with reference to the following non-limiting examples.

Example One

A left anterior descending (LAD) artery ligation procedure was performed to experimentally induce acute myocardial infarction in C57BL6 mice. If in situ sensing is to be achieved within the subcutaneous space, such as within the flank, the intended cardiac targets traditionally measured in serum must be detectable in the subcutaneous space. Serum levels of cardiac biomarkers after acute MI are well characterized in the existing literature, but their extravasation to the subcutaneous flank had not previously warranted study.

Figure 2:
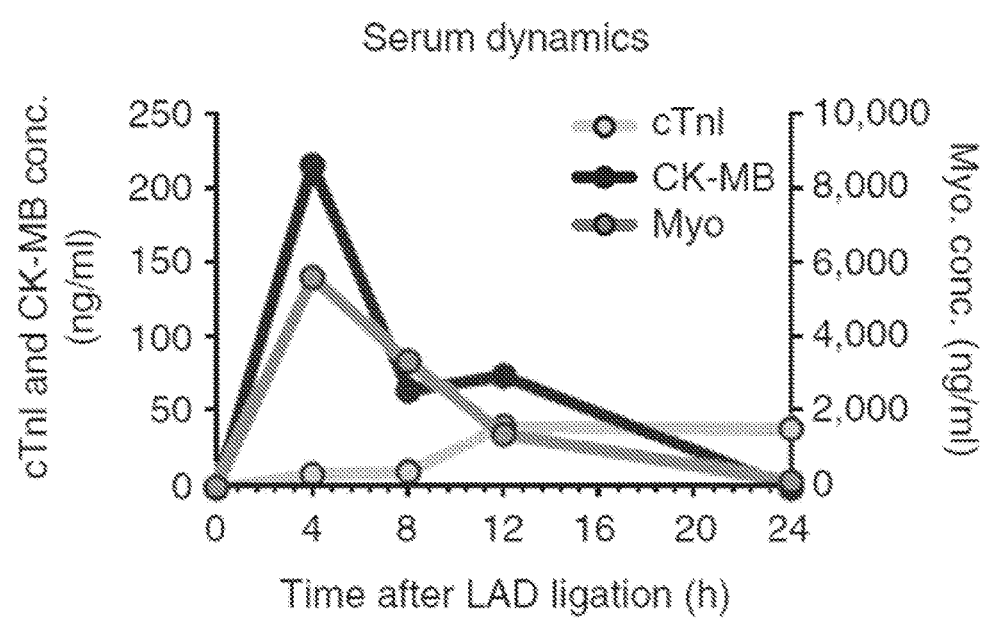
FIG. 2 is a graph, illustrating cTnI, myoglobin, and CK-MB serum profiles after LAD ligation measured using ELISA.
Figure 3:
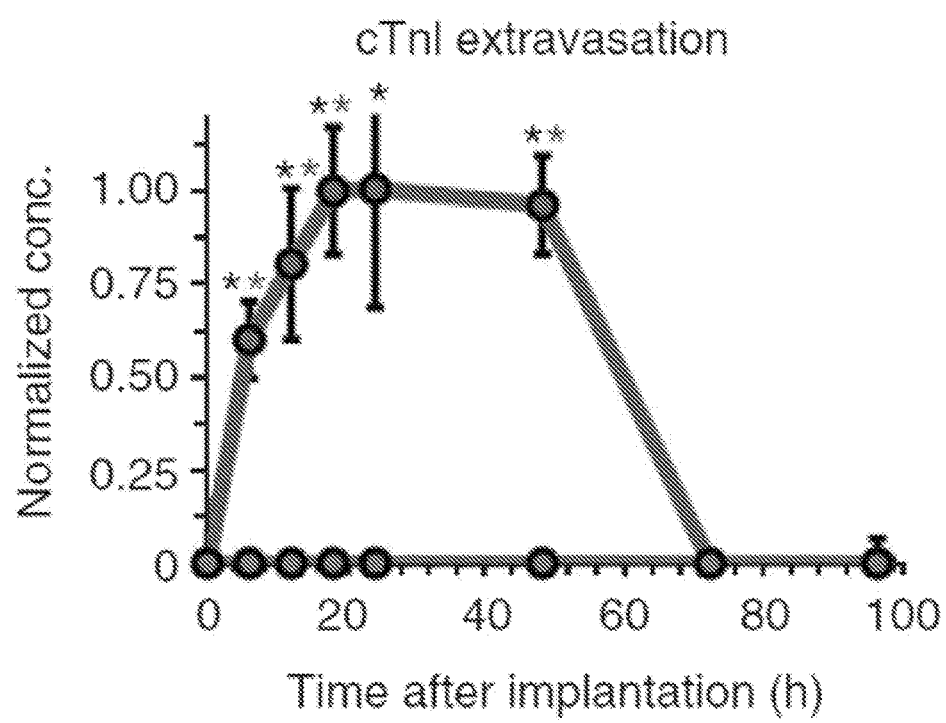
FIG. 3 is a graph, illustrating cTnI extravasation for control, sham, and MI experimental conditions measured using ELISA.
Figure 4:
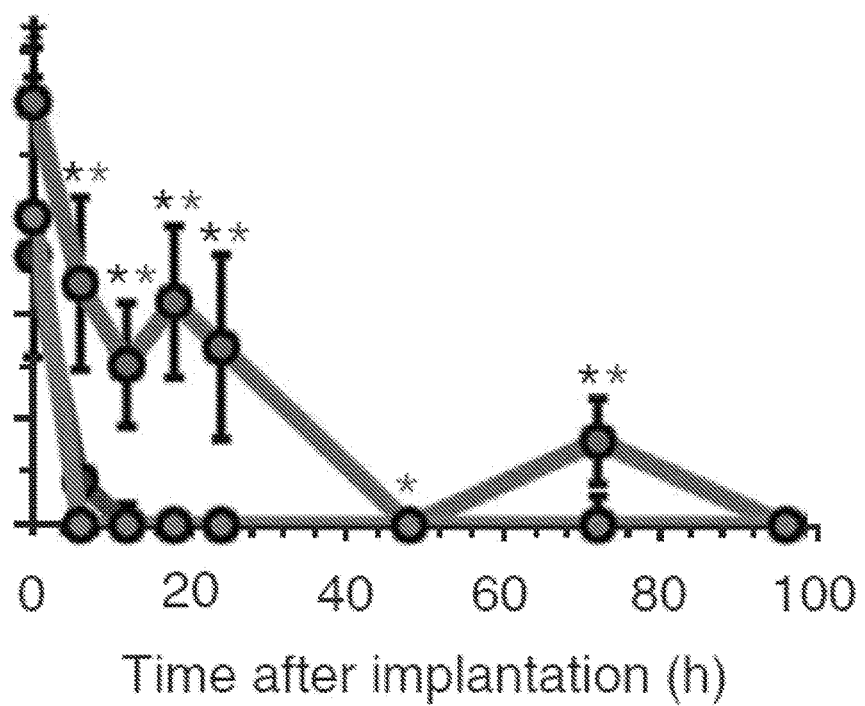
FIG. 4 is a graph, illustrating myoglobin extravasation for control, sham, and MI experimental conditions measured using ELISA.
Figure 5:
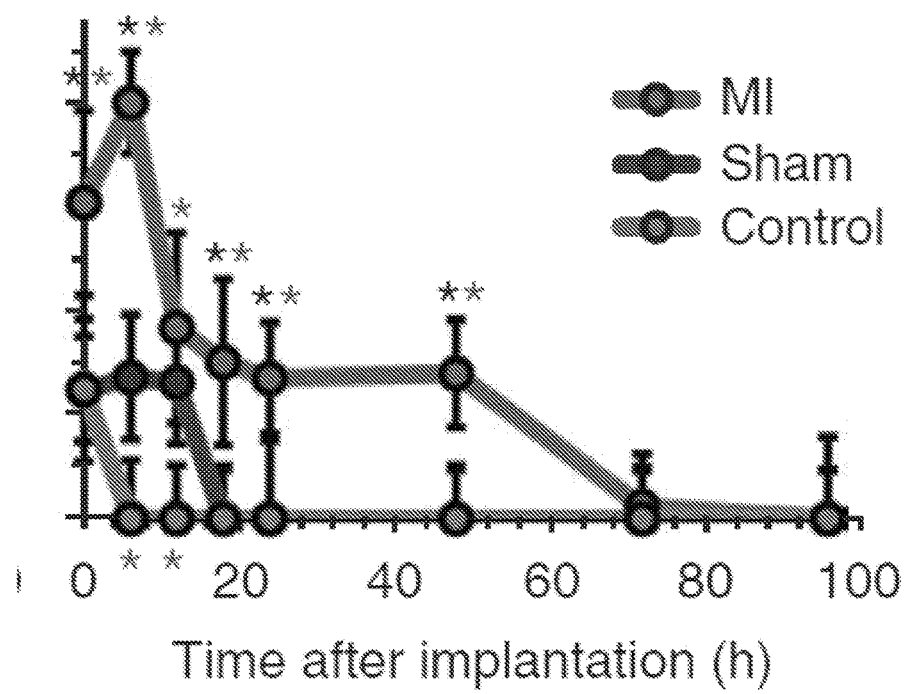
FIG. 5 is a graph, illustrating CK-MB extravasation for control, sham, and MI experimental conditions measured using ELISA.

Extravasation dynamics was experimentally determined under three conditions: MI, sham and control. Whereas MI groups received sensor implantation, thoracotomy and LAD ligation, sham groups received sensor implantation and thoracotomy but no LAD ligation. Control groups received sensor implantation only. The results, which demonstrate evidence of cardiac biomarker extravasation from serum to the subcutaneous space, are illustrated in FIGS. 2-5. FIG. 2 illustrates cTnI, myoglobin and CK-MB serum profiles after LAD ligation are within the range of literature results and confirm the validity of the MI model used. Approximately 0.5 ml of blood was drawn from each subject, the serum extracted by centrifugation and biomarker levels measured by enzyme-linked immunosorbent assay (ELISA) at the indicated times after LAD ligation. The results are illustrated averages (n=4), with error bars omitted for uncluttered visualization. As illustrated in FIGS. 2-5, each biomarker extravasates, with MI groups exhibiting significantly elevated concentrations, as compared to the corresponding control and sham groups. Presumably, implantation-induced injury caused the low initial cTnI in the setting of high initial myoglobin and CK-MB. The similarity between sham and control groups indicates that any thoracotomy-induced biomarker release is not significantly 'visible' in the sensor implant site. Extravasate samples were obtained by flushing the flank with 1 ml PBS at the indicated times after LAD ligation and measured using ELISA. Values are normalized within each panel to the maximum measured concentration. Results are averages ±s.e.m. (n=4, normalized); P<0.05 is indicated by black asterisks between MI/sham, red asterisks between MI/control and green asterisks between sham/control.

These results confirmed that the subcutaneous space is a viable site for cardiac biomarker detection, as biomarker elevations in the MI group differed significantly (P<0.05) from the sham and control groups. It should therefore be possible to distinguish between the experimental conditions based on measurements acquired from implanted sensors. There are, however, some initial elevations in myoglobin and CK-MB for the control and sham groups that the sensors are expected to detect. Open chest surgery and subcutaneous device implantation cause substantial noncardiac injury. The early behaviors of these biomarkers are consistent with their differing specificities for cardiac injury; cTnI is highly specific to cardiac damage, but CK-MB is less specific and myoglobin is a marker of general muscle damage. The fact that myoglobin and CK-MB are elevated in the control groups suggests local implantation-induced trauma will be visible to the implanted sensors. No significant difference can be found between the sham and control groups for any biomarker, suggesting that thoracotomy-induced trauma should not affect the in situ sensor response.

The movement of protein biomarkers from the circulation to the subcutaneous space should depend on the chemical properties of the specific biomarker as well as the vascularization and morphology of the implant site. The reliability of subcutaneously implanted sensors may be limited by these factors. Nonetheless, there is little delay seen here between the peaks in the accumulation of serum (FIG. 2) and extravasate (FIGS. 3-5) biomarkers. Rapid subcutaneous availability of these biomarkers, coupled with a sufficiently rapid sensor response, should enable potential applications of MI detection using this technology. The samples were obtained by flushing the subcutaneous space with 1 ml PBS and were assayed by ELISA.

Example Two

Antibody-antigen binding can provide an extremely strong noncovalent interaction. Antibody-based magnetic relaxation sensors were tested to determine whether the bonding may be irreversible and to determine the degree of $T_2$ change corresponding to the cumulative analyte exposure.

Sensors were constructed having functionalized superparamagnetic particles, encapsulated within discrete sensors and calibrated in vitro, to measure cumulative exposure to analyte in vitro. NanoMag-CLD superparamagnetic iron oxide nanoparticles (50 nm) with amine-terminated dextran shells (MicroMod) were coupled with monoclonal antibody against goat IgG (Meridian Life Sciences) using the method described in Josephson, L., Tung, C. H., Moore, A. & Weissleder, R. High-efficiency intracellular magnetic labeling with novel superparamagnetic-Tat peptide conjugates. *Bioconjug. Chem.* 10, 186-191 (1999). These particles were then derivatized against specific targets by incubation with goat-produced polyclonal antibodies against cTnI (BiosPacific), myoglobin (BiosPacific) and CK-MB (BiosPacific). Unless otherwise specified, particles were suspended in PBS with 1% BSA (Sigma-Aldrich) and 0.1% penicillin-streptomycin (Invitrogen) to minimize bacterial contamination and nonspecific adsorption.

Derivatized particles were encapsulated within small diffusion devices. Polycarbonate diffusion membranes (SPI Supplies) were affixed by double-sided adhesive to one side of high-density polyethylene cylinders (thickness=1.6 mm, inner diameter=4.1 mm, outer diameter=7.9 mm). The opposing end was closed off by single-sided adhesive (3M) after the reservoir was filled with 25 μl particle solution. Devices (n=6 per animal) were implanted subcutaneously in the flank. The animals were euthanized and the devices explanted for single-sided relaxometry at specified time points. Devices were sealed with single-sided adhesive and replaced in the implant site for imaging.

Figure 6:
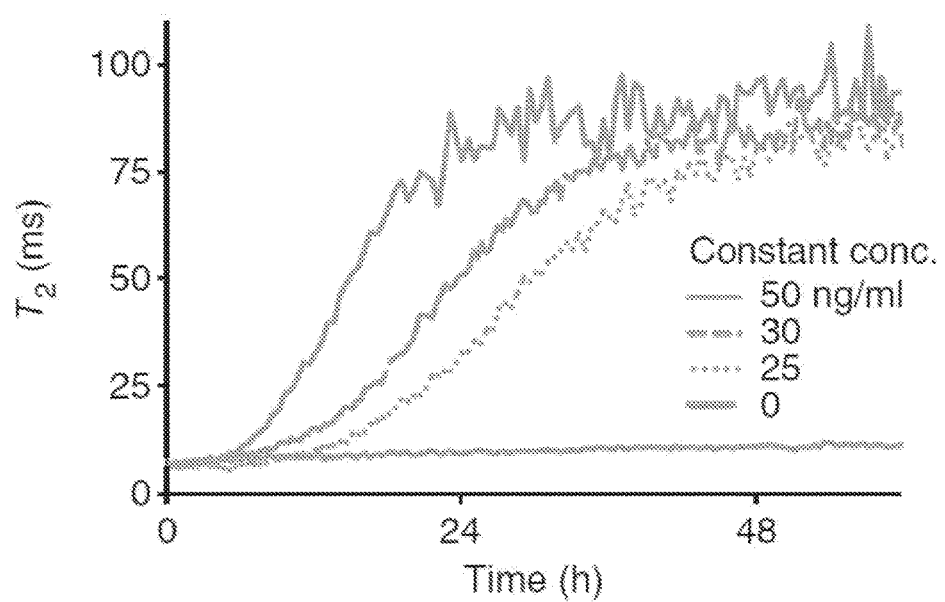
FIG. 6 is a graph, illustrating sensor saturation with constant environmental concentration profiles.

The sensors were exposed to four different constant myoglobin concentrations to investigate the integrative capacity of antibody-based magnetic relaxation sensors. As illustrated in FIG. 6, the overall response rate is proportional to the concentration outside the device, demonstrating that the sensor behavior is dominated by diffusion transport into the device reservoir. The sensor devices were maintained in a constant concentration of myoglobin solution and the relaxation time $T_2$ was measured every 20 min. The time to saturation depends on the concentration. All of the devices, with the exception of the control, show a similar response and saturate at the same $T_2$ value. The total exposure of the device to myoglobin (measured in units of [μg·h/ml]) is defined as the area under the concentration versus time curve up until the measurement time.

Figure 7:
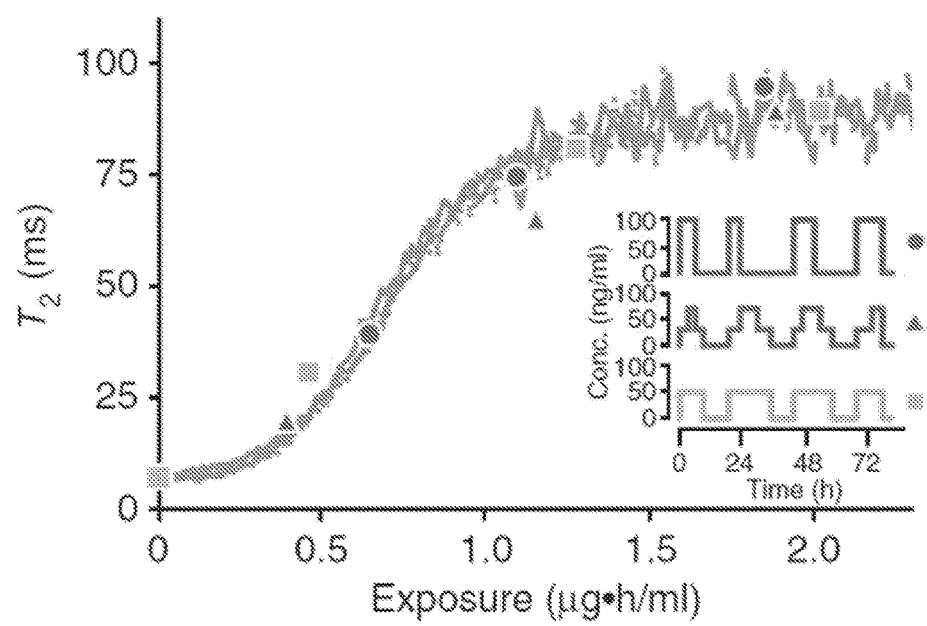
FIG. 7 is a graph, illustrating the sensor saturation with various temporal concentration profiles (shown inset).

Exposure may be defined the following formula:

$$E(t_m) = \int_{t=0}^{t_m} C(t) \, dt,$$

where C(t) is the analyte concentration as a function of time and $t_m$ is the time of measurement. Plotting the measured $T_2$ against exposure yields a single curve that is independent of the analyte concentration and verifies that the sensors operate as dosimeters in a diffusion-limited regime (FIG. 7, solid and dotted lines). The diffusion occurs across the full area of the device reservoir and the devices saturate at ~1.5 μg·h/ml. The saturating exposure level can be tuned to the anticipated in vivo biomarker levels by adjusting the area available for diffusion. Reducing the diffusion area by half would, therefore, increase the saturating exposure by a factor of two.

Because physiologic biomarker levels often follow non-constant dynamic patterns, sensor response was studied for three time varying concentration profiles as shown in FIG. 7 (n=2). FIG. 7 illustrates a plot of $T_2$ versus the constant exposure profiles. The symbols represent the average $T_2$ of devices exposed to various temporal concentration profiles shown inset. The curves and symbols lie on top of each other, demonstrating that the response depends exclusively on exposure. Most points have deviations smaller than the symbol size. Measurements were made after several hours of incubation at zero concentration.

These profiles simulate transient biomarker release when the instantaneous biomarker concentration at the time of measurement is zero. The sensor signal persists after the analyte is no longer present, and the measurements (FIG. 7, data points) coincide with the measured $T_2$ versus exposure profile (FIG. 7, solid and dotted lines). The results from prolonged exposure to constant and transient concentration profiles indicate that the biosensors ultimately function in a manner analogous to radiation dosimeters; they report consistent $T_2$ changes independent of the biomarker exposure profile.

The measurement of cumulative analyte release could be useful in detecting biomarker concentrations that are below the level of detection of blood-draw assays. This property also limits antibody-functionalized sensors to fixed lifetimes reached when the binding sites are saturated. Cumulative sensors can thus be used for finite durations, generally requiring engineering of the particles and devices to match the chosen application's required sensitivity and lifetime.

Figure 8:
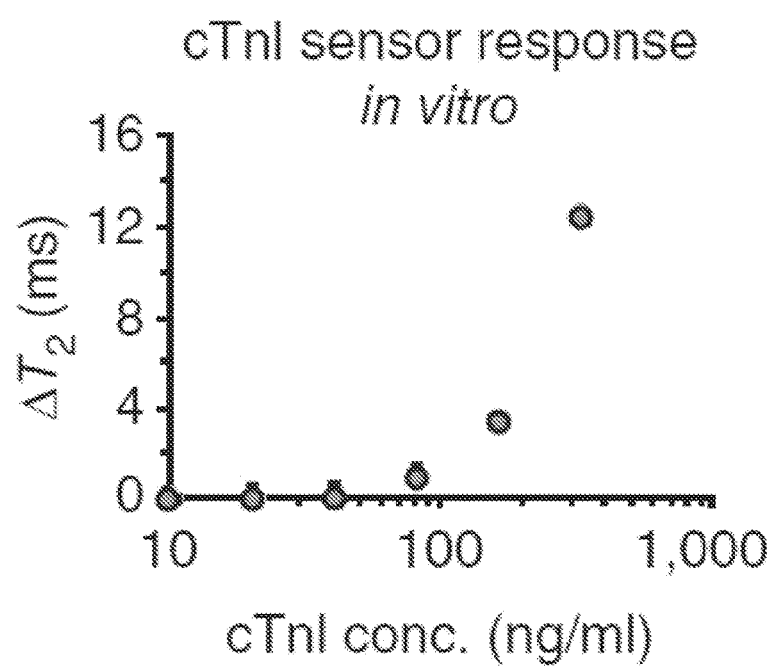
FIG. 8 is a graph, illustrating a cTnI sensor response in vitro as a function of cTnI concentration.
Figure 9:
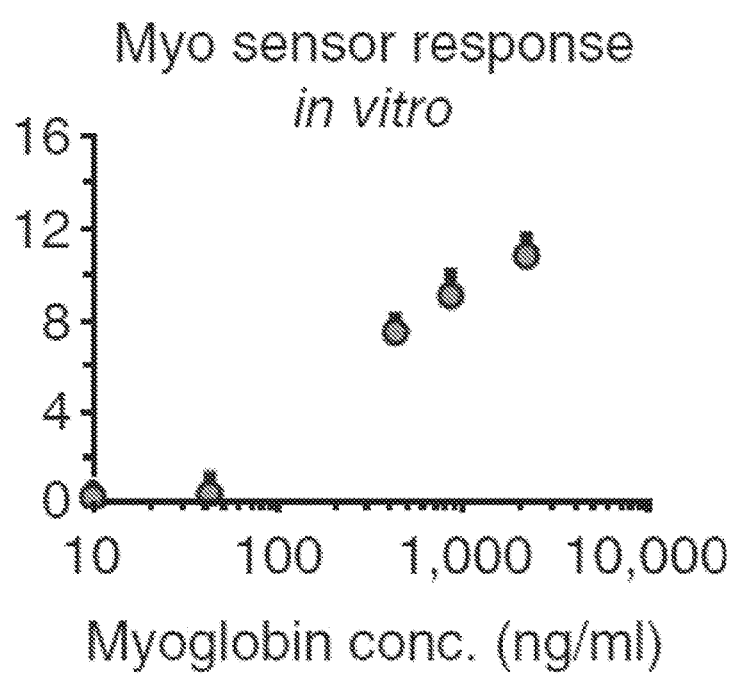
FIG. 9 is a graph, illustrating a myoglobin sensor response in vitro as a function of myoglobin concentration.
Figure 10:
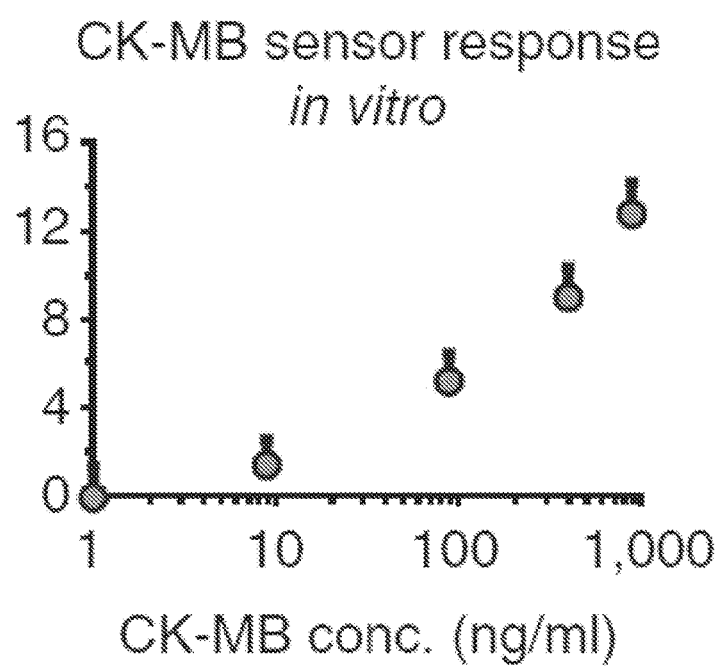
FIG. 10 is a graph, illustrating a CK-MB sensor response in vitro as a function of CK-MB concentration.

As illustrated in FIGS. 8-10, sensor response as a function of analyte concentration was calibrated to match expected in vivo concentrations. The measurements were acquired after an incubation time of 72 h for cTnI and 24 h for myoglobin and CK-MB sensors to match the expected duration of elevation for the respective biomarkers. Results are averages ±95% confidence intervals (n=4).

Example Three

Figure 11:
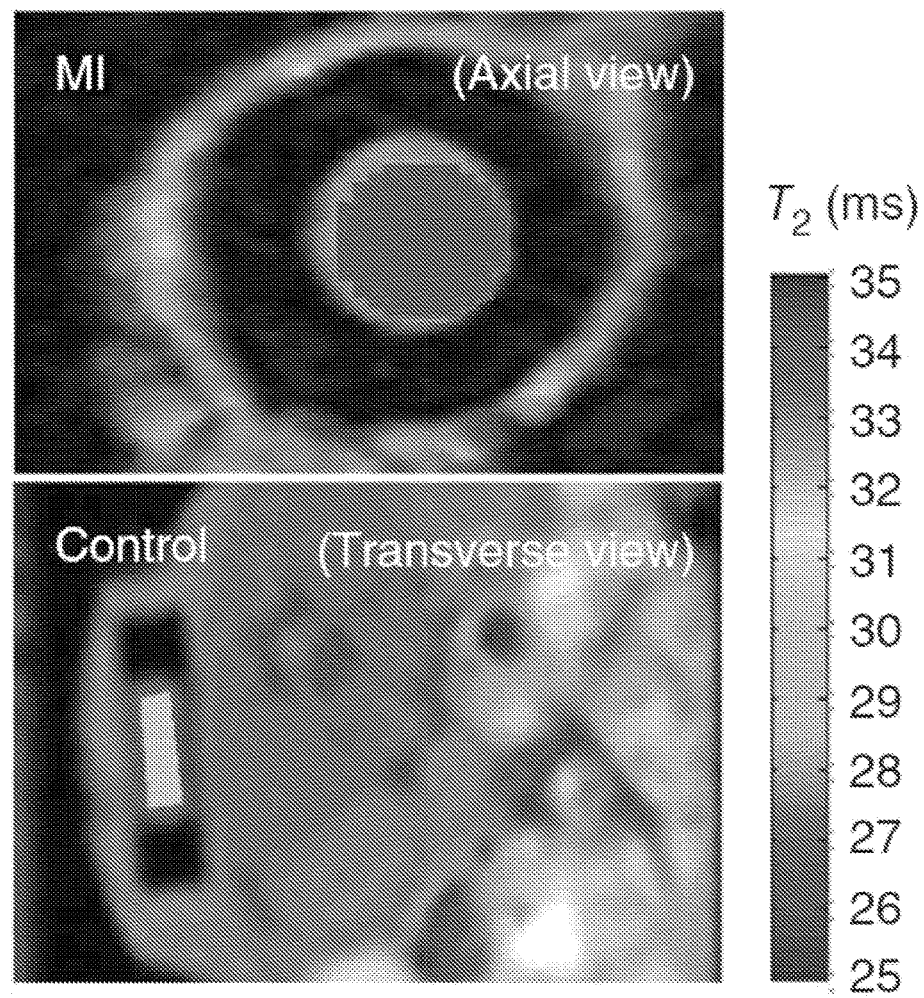
FIG. 11 is a graph, illustrating axial and transverse views of sensors with $T_2$-weighted images using MRI-based in situ measurements.

Sensors specific for each biomarker were implanted subcutaneously in the flanks of animals from the MI, sham and control groups. Because it is possible that the sensors might be acutely exposed to intravascular fluid as a result of surgery-induced capillary disruption, sensors in all three (MI, sham, control) groups were therefore implanted before any further surgery so that their acute post-implant exposures did not vary between groups. Any differences between the three groups can therefore be attributed to true biomarker extravasation. As illustrated in FIG. 11, in situ MRI measurements demonstrated that the sensors can be interrogated at the implant site. A $T_2$ map (color bar on the right) superimposed on $T_2$-weighted images of myoglobin sensors demonstrates the feasibility of MRI-based in situ measurements after 24 h implantation with (MI) or without (control) concomitant LAD ligation at the time of sensor implantation. The images show that the sensors can be measured in either the axial or the transverse plane, and coloration may be used to distinguish the level of cumulative exposure of a sensor to a biomarker.

Figure 12:
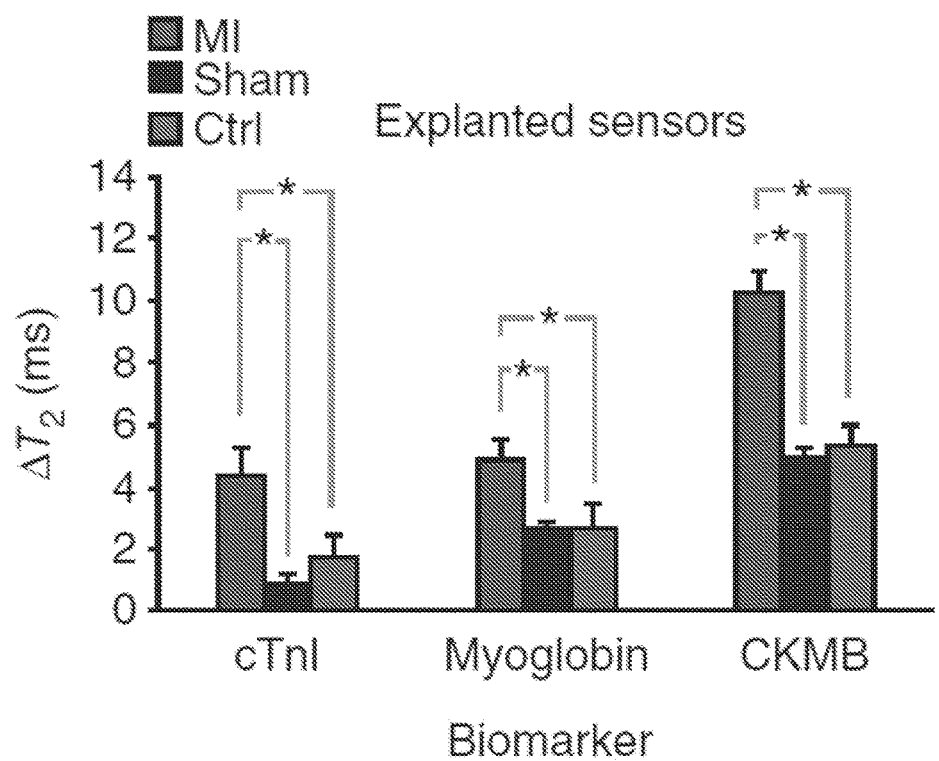
FIG. 12 is a chart, illustrating $T_2$ measurements of explanted sensors as measured by single-sided proton relaxometry.

Most measurements were obtained from explanted sensors using a single-sided relaxometer. Despite the limited sensitivity of the single-sided system, $T_2$ increases of the MI over the sham and control groups for all three biomarkers are evident as illustrated in FIG. 12. Wilcoxon rank-sum two-sided tests give significant P values (P<0.05) for cross comparisons between the MI and control groups, and between the MI and sham groups but not between sham and control groups. The elevations in levels of myoglobin and CK-MB above baseline in the sham and control groups reflect noncardiac injury caused by the initial surgical procedure. Implanted magnetic relaxation sensors functionalized against IgG alone showed negligible increases in $T_2$.

Figure 13:
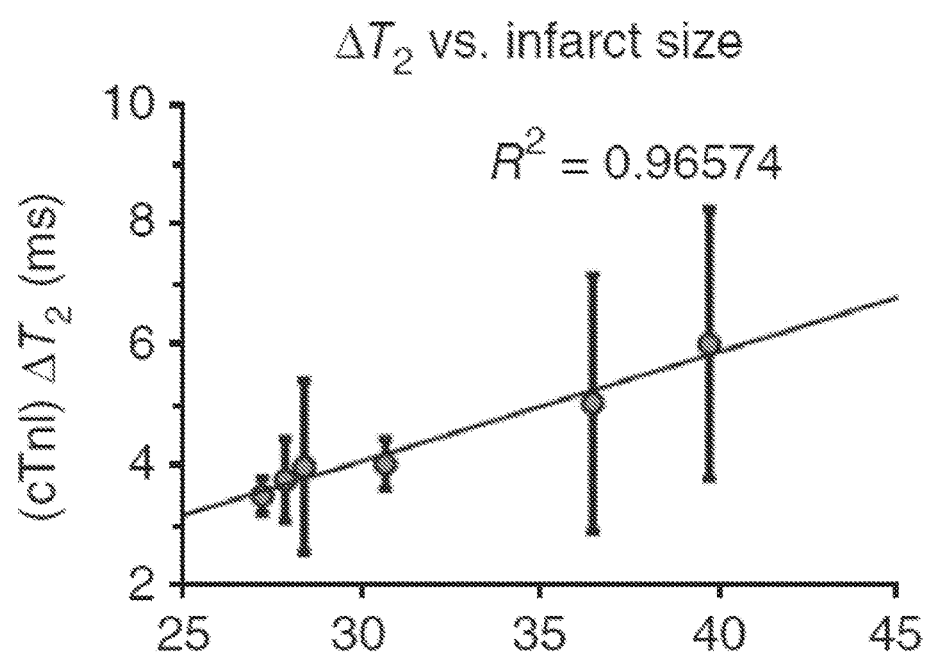
FIG. 13 is a graph, illustrating $T_2$ change of the explanted cTnI sensor disaggregated into the individual subjects and replotted as a function of infarct size.
Figure 14:
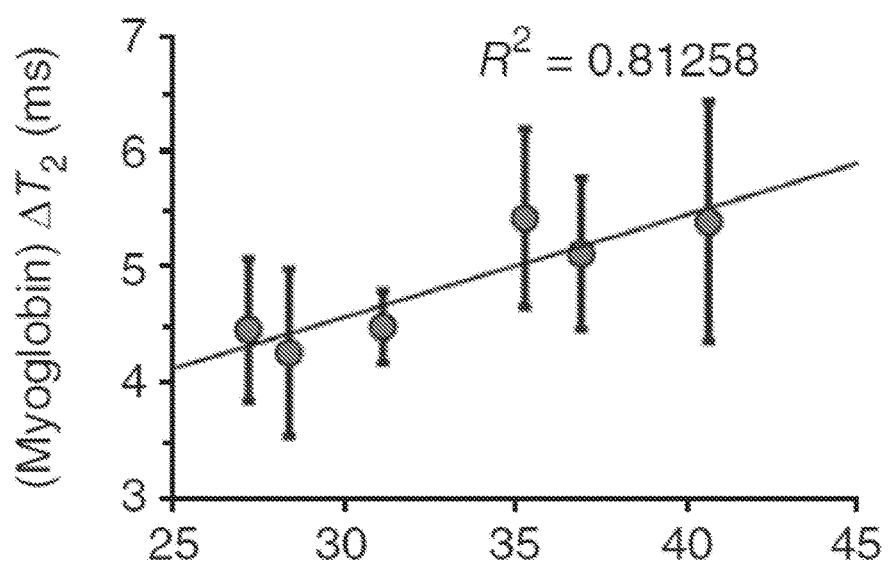
FIG. 14 is a graph, illustrating $T_2$ change of the explanted myoglobin sensor disaggregated into the individual subjects and replotted as a function of infarct size.
Figure 15:
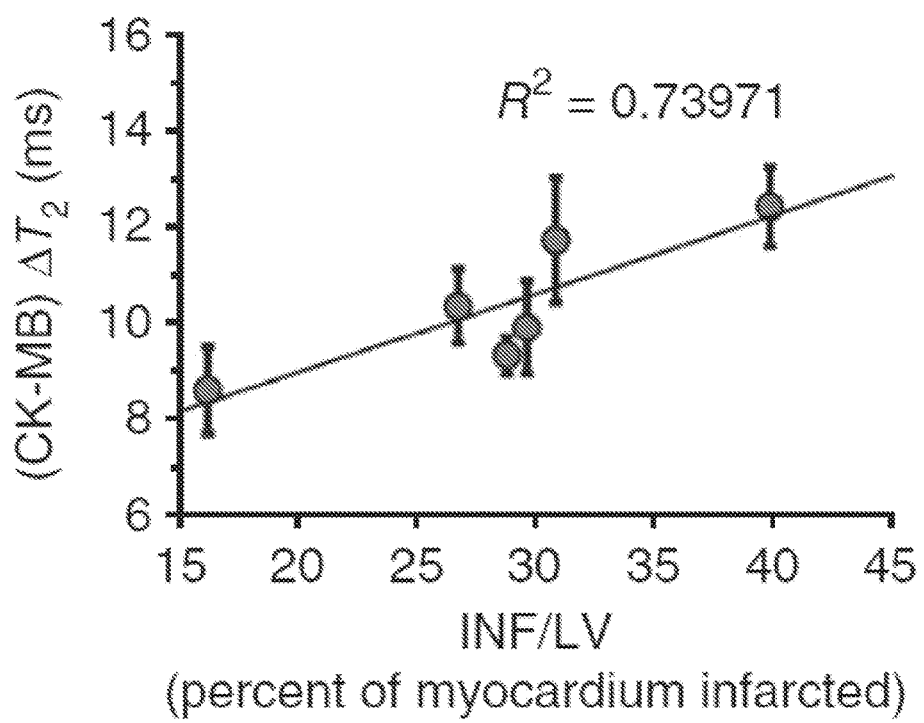
FIG. 15 is a graph, illustrating $T_2$ change of the explanted CK-MB sensor disaggregated into the individual subjects and replotted as a function of infarct size.

The infarct zone can be visualized through 2,3,5-triphenyltetrazolium chloride staining and objectively quantified as the fraction of left ventricular volume. The cumulative release of cardiac biomarkers should be directly proportional to the magnitude of infarction, as the biomarkers are functional proteins directly released from the ischemic tissue. FIGS. 13-15 illustrate a comparison of sensor readings with infarct size shows a consistent trend for all three biomarkers, despite the relatively large errors. The cumulative release of biomarkers from the infarcted myocardium generates the final $T_2$ sensor value. The capability to quantitatively measure infarct size has important implications for risk stratification of MI patients. This factor usually measured indirectly in the clinic through functional tests or imaging, can be directly quantified by the implantable sensors described here. Sensor response differs markedly between MI and sham/control groups, and its magnitude correlates with the extent of infarction. Results are averages ±95% confidence intervals (n=6 sensors/subject).

Example Four

Figure 16:
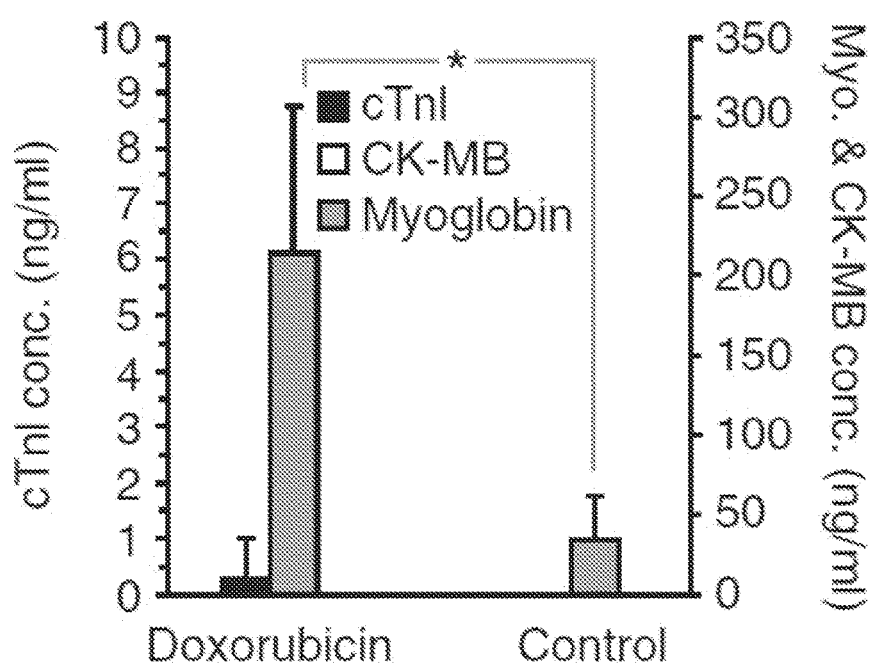
FIG. 16 is a chart, illustrating data from experiments using sensors to detect the cardiotoxic effect of the drug Doxorubicin measured by ELISA.
Figure 17:
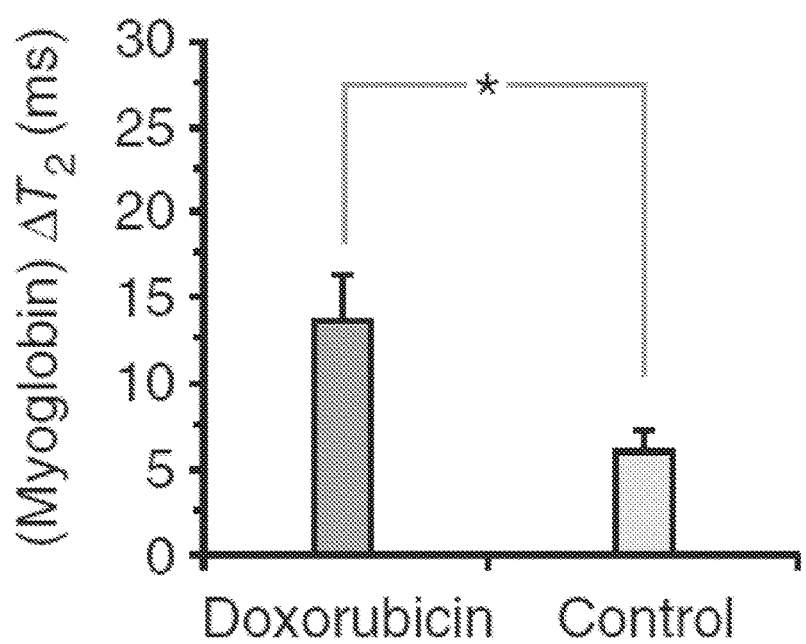
FIG. 17 is a chart, illustrating data from experiments using sensors to detect the cardiotoxic effect of the drug Doxorubicin measured by change in $T_2$ of explained sensors.

The application of the sensors to discern drug cardiotoxicity was also studied. Doxorubicin is a potent anthracycline antibiotic that has found wide clinical use as a cancer chemotherapeutic. Its cardiotoxic effects are well known; after administration, patients exhibit dose-dependent loss of cardiac myocytes accompanied by serum cardiac biomarker elevation. It was confirmed that serum myoglobin increases after doxorubicin administration in a murine model (as illustrated in FIG. 16), although at an order of magnitude lower concentration than after acute MI ($10^2$ ng/ml versus $10^3$ ng/ml). Myoglobin sensors were thus left in vivo for 72 h after implantation (as opposed to 24 h for acute MI). The results, illustrated in FIG. 17 show a clear distinction in sensor $T_2$ between the experimental and control groups, thus validating sensor efficacy in assaying drug cardiotoxicity. These sensors may therefore be used to establish the cardiac side effects of novel pharmaceuticals.

While the present invention may be embodied in many different forms, disclosed herein are specific illustrative embodiments thereof that exemplify the principles of the invention. It should be emphasized that the present invention is not limited to the specific embodiments illustrated.

We claim:

1. An implantable magnetic relaxation sensor comprising:
   superparamagnetic nanoparticles functionalized with one or more agents that irreversibly bond with a biomarker of interest;
   wherein the sensor is configured for minimally-invasive implantation into a human or animal; and
   wherein the sensor is configured to operate as a dosimeter to indicate the implanted sensor's cumulative exposure to the biomarker of interest with a single reading of the sensor by analysis using magnetic resonance relaxometry.

2. The sensor of claim 1, wherein the one or more agents comprise an antibody.

3. The sensor of claim 2, wherein the one or more agents comprise antibodies for myoglobin, cTnI, CK-MB, or a combination thereof.

4. The sensor of claim 3, wherein the biomarker of interest is myoglobin, cTnI, CK-MB, or a combination thereof; and wherein the sensor is configured to indicate the sensor's cumulative exposure to myoglobin, cTnI, CK-MB, or a combination thereof after the sensor has been implanted and the sensor is analyzed using magnetic resonance relaxometry.

5. The sensor of claim 4, wherein the sensor is sensitive to cTnI in a range of 10-100 ng/mL.

6. The sensor of claim 4, wherein the sensor is sensitive to myoglobin in a range of 100 ng/mL to 1 μg/mL.

7. The sensor of claim 4, wherein the sensor is sensitive to CK-MB in a range of 100 ng/mL to 1 μg/mL.

8. The sensor of claim 1, wherein the nanoparticles comprise iron oxide.

9. The sensor of claim 1, further comprising a sensor body having at least one reservoir, wherein the nanoparticles are contained within the at least one reservoir.

10. The sensor of claim 9, wherein the nanoparticles are retained within the at least one reservoir by one or more size-exclusion membranes.

11. An implantable magnetic relaxation sensor comprising:

superparamagnetic nanoparticles functionalized with one or more antibodies that irreversibly bond with myoglobin, cTnI, CK-MB, or a combination thereof;

wherein the sensor is configured to operate as a dosimeter to indicate the sensor's cumulative exposure to myoglobin, cTnI, CK-MB, or a combination thereof with a single reading of the sensor by analysis using magnetic resonance relaxometry after the sensor has been implanted, and wherein the sensor comprises a sensor body having at least one reservoir, wherein the nanoparticles are contained within the at least one reservoir.

12. The sensor of claim 11, wherein the nanoparticles comprise iron oxide.

13. The sensor of claim 11, wherein the nanoparticles are retained within the at least one reservoir by one or more size-exclusion membranes.

14. The sensor of claim 11, wherein the sensor is sensitive to cTnI in a range of 10-100 ng/mL.

15. The sensor of claim 11, wherein the sensor is sensitive to myoglobin in a range of 100 ng/mL to 1 μg/mL.

16. The sensor of claim 11, wherein the sensor is sensitive to CK-MB in a range of 100 ng/mL to 1 μg/mL.

* * * * *